United States Patent
De Santa Barbara et al.

(10) Patent No.: US 11,300,568 B2
(45) Date of Patent: Apr. 12, 2022

(54) METHODS FOR THE DIAGNOSIS AND TREATMENT OF GASTROINTESTINAL STROMAL TUMORS

(71) Applicants: INSERM (INSTITUT NATIONAL DE LA SANTE ET DE LA RECHERCHE MEDICALE), Paris (FR); UNIVERSITE DE MONTPELLIER, Montpellier (FR); CENTRE NATIONAL DE LA RECHERCHE SCIENTIFIQUE, Paris (FR)

(72) Inventors: Pascal De Santa Barbara, Montpellier (FR); Sandrine Faure-De Santa Barbara, Montpellier (FR)

(73) Assignees: INSERM (INSTITUT NATIONAL DE LA SANTE ET DE LA RECHERCHE MEDICALE, Paris (FR); UNIVERSITE DE MONTPELLIER, Montpellier (FR); CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 49 days.

(21) Appl. No.: 16/077,172

(22) PCT Filed: Feb. 10, 2017

(86) PCT No.: PCT/EP2017/052979
§ 371 (c)(1),
(2) Date: Aug. 10, 2018

(87) PCT Pub. No.: WO2017/137545
PCT Pub. Date: Aug. 17, 2017

(65) Prior Publication Data
US 2019/0049454 A1 Feb. 14, 2019

(30) Foreign Application Priority Data

Feb. 11, 2016 (EP) .................................. 16305159

(51) Int. Cl.
| | |
|---|---|
| *A61K 48/00* | (2006.01) |
| *G01N 33/574* | (2006.01) |
| *C07K 14/47* | (2006.01) |
| *A61K 31/00* | (2006.01) |
| *A61P 35/00* | (2006.01) |
| *G01N 33/50* | (2006.01) |

(52) U.S. Cl.
CPC ....... *G01N 33/57446* (2013.01); *A61K 31/00* (2013.01); *A61P 35/00* (2018.01); *C07K 14/47* (2013.01); *G01N 33/5011* (2013.01); *G01N 2500/04* (2013.01); *G01N 2800/50* (2013.01)

(58) Field of Classification Search
None
See application file for complete search history.

(56) References Cited

FOREIGN PATENT DOCUMENTS

| | | |
|---|---|---|
| EP | 2 985 345 A1 | 2/2016 |
| WO | 2014/168064 A1 | 10/2014 |

OTHER PUBLICATIONS

Xu et al (Asian Journal of Pharmaceutical Sciences, 2015, vol. 10, pp. 1-12).*
E.N. Wakeling et al: "Lix1 Knockout Mouse Does Not Exhibit Spinal Muscular Atrophy Phenotype", Journal of Heredity., vol. 102, No. Suppl 1, pp. S32-S39, Aug. 16, 2011.
Markku Miettinen et al: "Gastrointestinal Stromal Tumors", Gastroenterology Clinics of North America., vol. 42, No. 2, pp. 399-415, Jun. 1, 2013.
Jennifer Mckey et al: "LIX1 regulates YAP1 activity and controls the proliferation and differentiation of stomach mesenchymal progenitors", BMC Biology, vol. 25, No. 1, p. 402, Apr. 28, 2016.

* cited by examiner

*Primary Examiner* — Celine X Qian
(74) *Attorney, Agent, or Firm* — WC&F IP

(57) ABSTRACT

The present invention relates to the diagnosis of gastrointestinal stromal tumors (GISTs). The present invention also relates to methods and compositions for the treatment of gastrointestinal stromal tumors (GISTs).

4 Claims, 6 Drawing Sheets

A

METHODS FOR THE DIAGNOSIS AND TREATMENT OF GASTROINTESTINAL STROMAL TUMORS

FIELD OF THE INVENTION

Figure 1:
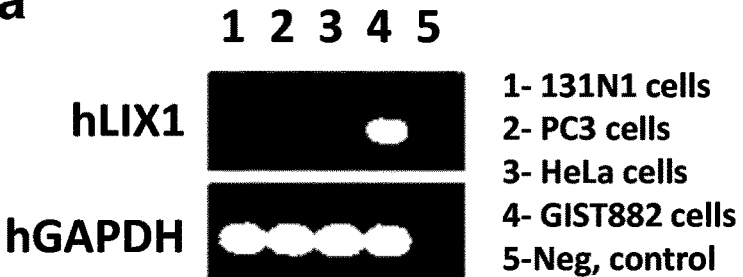
Figure 1:
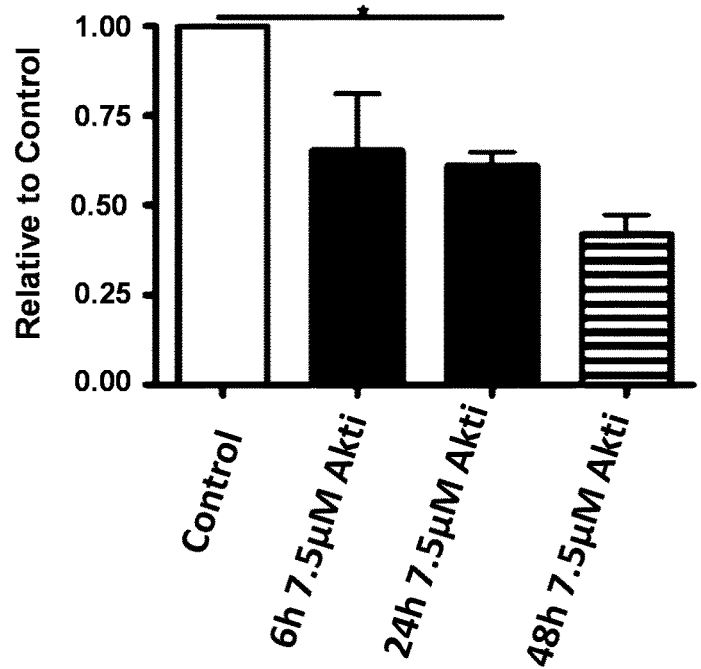
Figure 1:
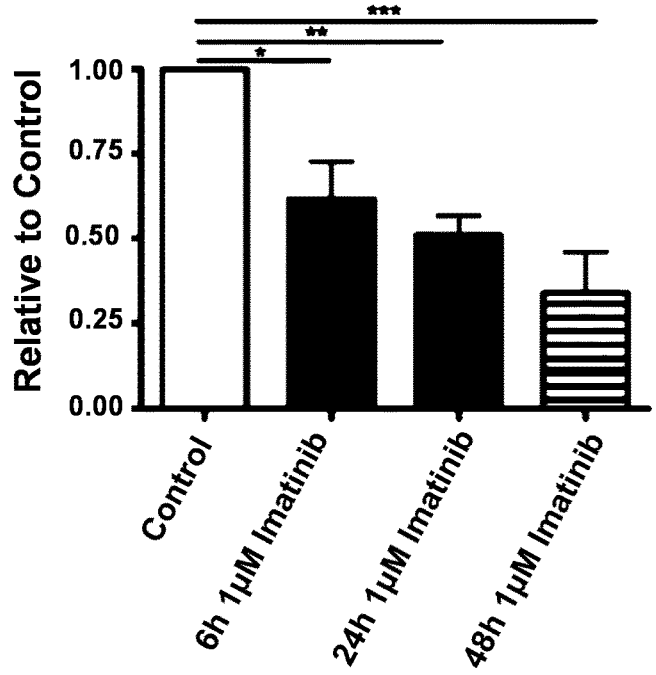

The present invention relates to the diagnosis of gastrointestinal stromal tumors (GISTs). The present invention also relates to methods and compositions for the treatment of gastrointestinal stromal tumors (GISTs).

BACKGROUND OF THE INVENTION

During development, the gastrointestinal tract arises from a primary tube composed of mesoderm and endoderm. The mesoderm gives rise to the digestive mesenchyme, which in turn differentiates into multiple tissues, namely the submucosa, the interstitial cells of Cajal (ICCs), and the smooth muscle cells (SMCs) (Wallace and Burns, 2005). In the adult musculature, mesenchyme-derived cells demonstrate high plasticity, a quality often associated with high neoplastic risk (Nieto, 2013). Gastrointestinal stromal tumors (GISTs) are the most common mesenchymal neoplasms of the gastrointestinal tract (Corless et al, 2011). GIST cells are mostly characterized by the presence of activating mutations in one of two genes that code for closely related tyrosine kinases, namely KIT (75-80%) and platelet-derived growth factor receptor alpha (PDGFRA) (5-10%) (Hirota et al, 1998; Heinrich et al, 2003). Thus, the common treatment for unresectable or metastatic GISTs is the tyrosine kinase inhibitor imatinib-mesylate (Joensuu et al, 2001; Tuveson et al, 2001). Since its introduction in 2002, imatinib has increased GIST patient survival from 30% after 1 year to 50% after 5 years (Sleijfer et al, 2007). Nevertheless, resistance to imatinib is increasing and complete remissions are rare, highlighting the necessity to identify additional therapeutic targets (Renouf et al, 2009).

Because tumor progression has often been associated with the re-expression of markers of immature tissue (Dormoy et al, 2012), developmental studies have proven to be a reliable source for the identification of new tumoral markers (Bertrand et al, 2012). In this context, it has recently been shown that genes involved in the development and plasticity of SMCs demonstrate abnormal expression in GISTs (Hapkova et al, 2013; Notarnicola et al, 2012). Perseverance in this strategy could lead to a better understanding of the origins of GISTs and eventually to a more thorough molecular understanding of GIST physiopathology.

The process of digestive mesenchyme development into SMCs is commonly decomposed into two major steps (Gabella, 2002). First, mesenchymal progenitor cells enter a determination program (that we will refer to as SMC determination), mainly characterized by the early expression of alpha smooth muscle actin ($\alpha$SMA). Later during development, determined SMCs differentiate into SMCs (that we will refer to as SMC differentiation), visualized by the expression of contractile proteins, such as CALPONIN. The RNA-binding protein RBPMS2 has recently been demonstrated as a regulator of SMC differentiation and plasticity (Notarnicola et al, 2012; Sagnol et al, 2014). However, little is known about the molecular mechanisms that drive the earlier progression of mesenchyme progenitor cells into determined SMCs. Using a microarray approach to identify candidate genes in digestive SMC development, the inventors screened for genes that demonstrated higher expression at the earliest stages of stomach development (E5). This allowed us to identify Limb Expression 1 (LIX1), a gene coding for a 281-amino acid protein. Although predictive in silico studies have shown that LIX1 has a double-stranded RNA binding domain, suggesting that it could be involved in RNA processing (Bando et al, 2011), no cellular function of LIX1 has yet been described. Interestingly, chicken (*Gallus gallus*) LIX1, first identified in a gene expression screen to identify new markers of limb development, was shown to be expressed in the anterior and posterior intestinal portals, the early buds that will invaginate to give rise to the primary intestinal tube (Swindell et al, 2001). Moreover, the insect homolog of LIX1, lowfat, has been characterized, through its interaction with the atypical cadherins fat and dachsous, as a component of the Hippo pathway (Mao et al, 2009; Bando et al, 2011). Interestingly, the Hippo pathway has been at the center of many studies regarding the regulation of the balance between cell proliferation and differentiation (Xie, 2012; An et al, 2013). Indeed, the Hippo core cascade of kinases is activated when proper cell density and organ size are reached, leading to the inhibitory Ser127-phosphorylation of the transcriptional coactivator YAP1 (Zhao et al, 2010; Halder and Johnson, 2011). This leads to decreased transcription of YAP1 mitogenic targets, resulting in a decrease in cell proliferation and entry into a more differentiated state (Halder, 2012).

In the present invention, the inventors investigate LIX1 function during digestive smooth muscle development. The inventors show that LIX1 is a novel marker of stomach mesenchymal progenitors and that its expression is strong and highly dynamic. The inventors show that LIX1 positively regulates cell proliferation and SMC determination. However, the inventors demonstrate that sustained LIX1 expression hinders the later step of SMC differentiation. Finally, the inventors show that LIX1 is expressed in GISTs and that high LIX1 expression is associated with poor patient prognosis.

SUMMARY OF THE INVENTION

The present invention relates to the diagnosis of gastrointestinal stromal tumors (GISTs). The present invention also relates to methods and compositions for the treatment of gastrointestinal stromal tumors (GISTs). The present invention also relates to a LIX1 inhibitor for use in the treatment of gastrointestinal stromal tumors (GISTs) in a subject in need thereof.

DETAILED DESCRIPTION OF THE INVENTION

The inventors investigated GIST physiopathology using the chick embryo as a model organism, human GIST samples and GIST cell lines. The inventors identified Limb Expression 1 (LIX1) as a unique marker of stomach mesenchymal progenitors. Using in vivo functional approaches, the inventors demonstrated that LIX1 is required for proper SMC determination. Furthermore, although sustained LIX1 expression resulted in an expanded determined SMC domain, SMC differentiation, the later step of SMC development, was hindered, demonstrating the requirement for a tight regulation of LIX1 expression during stomach mesenchyme development. To further investigate by which mechanisms LIX1 functions, the inventors used an in vitro heterologous cell culture approach and found that LIX1 induced YAP1 transcripts and stimulated cell proliferation at low cell density, whereas the pro-proliferation activity of LIX1 was abolished at high cell density. The inventors further demonstrated that LIX1 expression is abnormally high in human GIST samples, highlighting cell immaturity within GISTs. Moreover, high LIX1 expression is associated with unfavorable prognosis.

Altogether, the invention identifies LIX1 as a new marker of GISTs, and a new regulator of stomach mesenchyme differentiation, through its capacity to regulate YAP1 activity and density-dependent proliferation.

Therapeutic Method

Accordingly, the present invention relates to a LIX1 inhibitor for use in the treatment of gastrointestinal stromal tumors (GISTs) in a subject in need thereof.

As used herein, the term "subject" denotes a mammal. In a preferred embodiment of the invention, a subject according to the invention refers to any subject (preferably human) afflicted with gastrointestinal stromal tumors (GISTs).

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "gastrointestinal stromal tumors" or "GISTs" has its general meaning in the art and refers to any type of gastrointestinal stromal tumors (GISTs) such as revised in the World Health Organisation Classification and selected from the group: 8936/1 (http://www.pubcan.org/searchresults.php?action=search&icdo=8936/1 &id=600). The term "GISTs" also refers to tumors that occurs in the gastrointestinal (GI or digestive) tract, including the esophagus, stomach, gallbladder, liver, small intestine, colon, ampulla vater, rectum, omentum, anus, and lining of the gut. The term "GISTs" also relates to unresectable GISTs, metastatic GISTs and GISTs resistant to treatments such as imatinib treatment. The term "GISTs" also relates to GISTs characterized by the presence of activating mutations in at least one gene such as the tyrosine kinase KIT and platelet-derived growth factor receptor alpha (PDGFRA) (Hirota et al, 1998; Heinrich et al, 2003).

As used herein, the term "LIX1" has its general meaning in the art and refers to the Limb Expression 1, a member of RNA-Binding Protein family (Bando et al, 2011).

The term "LIX1 inhibitor" has its general meaning in the art and refers to a compound that selectively blocks or inactivates the LIX1. The term "LIX1 inhibitor" also refers to a compound that selectively blocks the binding of LIX1 to its RNA binding cites (such as YAP1). The term "LIX1 inhibitor" also refers to a compound able to prevent the action of LIX1 for example by inhibiting the LIX1 regulation of YAP1 activity and SMC proliferation. As used herein, the term "selectively blocks or inactivates" refers to a compound that preferentially binds to and blocks or inactivates LIX1 with a greater affinity and potency, respectively, than its interaction with the other sub-types of the RNA-Binding Protein family. Compounds that block or inactivate LIX1, but that may also block or inactivate other RNA-Binding Protein sub-types, as partial or full inhibitors, are contemplated. The term "LIX1 inhibitor" also refers to a compound that inhibits LIX1 expression. Typically, a LIX1 inhibitor compound is a small organic molecule, a polypeptide, an aptamer, an intra-antibody, an oligonucleotide or a ribozyme.

Tests and assays for determining whether a compound is a LIX1 inhibitor are well known by the skilled person in the art such as described in the Example.

In another embodiment, the LIX1 inhibitor of the invention is a compound inhibiting the LIX1 downstream effectors such as YAP1 inhibitors.

Accordingly, the present invention also relates to a YAP1 inhibitor for use in the treatment of gastrointestinal stromal tumors (GISTs) in a subject in need thereof.

The term "YAP1" has its general meaning in the art and refers to the Yes-Associated Protein, the key downstream regulator of the Hippo pathway. The term "YAP1" also relates to a transcriptional co-activator that mainly interacts with transcription factors of the TEAD family, which are essential in mediating YAP-dependent gene expression [13,14,15].

The term "YAP1 inhibitor" has its general meaning in the art and refers to compounds inhibiting the Hippo-YAP signaling pathway such as YAP1 expression inhibitors, YAP1 nuclear translocation inhibitors or YAP1 phosphorylation inhibitors. YAP1 inhibitors are well-known in the art as illustrated WO2013188138 and WO2013148198. Typically, a YAP1 inhibitor is a small organic molecule, a peptide, a polypeptide, an aptamer or an intra-antibody.

In one embodiment of the invention, the YAP1 inhibitors include inhibitors of the Hippo-YAP signaling pathway such as described in WO2013188138 and YAP1 inhibitors described in WO2013148198.

In one embodiment, the LIX1 inhibitor of the invention is an aptamer. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against LIX1 of the invention as above described, the skilled man in the art can easily select those blocking or inactivating LIX1.

In one embodiment, the LIX1 inhibitor of the invention is an LIX1 expression inhibitor.

The term "expression" when used in the context of expression of a gene or nucleic acid refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include messenger RNAs, which are modified, by processes such as capping, polyadenylation, methylation, and editing, and proteins (e.g., LIX1) modified by, for example, methylation, acetylation, phosphorylation, ubiquitination, SUMOylation, ADP-ribosylation, myristilation, and glycosylation.

An "inhibitor of expression" refers to a natural or synthetic compound that has a biological effect to inhibit the expression of a gene.

LIX1 expression inhibitors for use in the present invention may be based on antisense oligonucleotide constructs. Anti-sense oligonucleotides, including anti-sense RNA molecules and anti-sense DNA molecules, would act to directly block the translation of LIX1 mRNA by binding thereto and thus preventing protein translation or increasing mRNA degradation, thus decreasing the level of LIX1 proteins, and thus activity, in a cell. For example, antisense oligonucleotides of at least about 15 bases and complementary to unique regions of the mRNA transcript sequence encoding LIX1 can be synthesized, e.g., by conventional phosphodiester techniques and administered by e.g., intravenous injection or infusion. Methods for using antisense techniques for specifically alleviating gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as LIX1 expression inhibitors for use in the present invention. LIX1 gene expression can be reduced by contacting the subject or cell with a small double stranded RNA (dsRNA), or a vector or construct causing the production of a small double stranded RNA, such that LIX1 expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as LIX1 expression inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of LIX1 mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as LIX1 expression inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing LIX1. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Typically the inhibitors according to the invention as described above are administered to the subject in a therapeutically effective amount.

By a "therapeutically effective amount" of the inhibitor of the present invention as above described is meant a sufficient amount of the inhibitor for treating GISTs at a reasonable benefit/risk ratio applicable to any medical treatment. It will be understood, however, that the total daily usage of the inhibitors and compositions of the present invention will be decided by the attending physician within the scope of sound medical judgment. The specific therapeutically effective dose level for any particular subject will depend upon a variety of factors including the disorder being treated and the severity of the disorder; activity of the specific inhibitor employed; the specific composition employed, the age, body weight, general health, sex and diet of the subject; the time of administration, route of administration, and rate of excretion of the specific inhibitor employed; the duration of the treatment; drugs used in combination or coincidential with the specific inhibitor employed; and like factors well known in the medical arts. For example, it is well within the skill of the art to start doses of the inhibitor at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the inhibitor of the present invention for the symptomatic adjustment of the dosage to the subject to be treated. A medicament typically contains from about 0.01 mg to about 500 mg of the inhibitor of the present invention, preferably from 1 mg to about 100 mg of the inhibitor of the present invention. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the LIX1 inhibitor of the present invention is administered to the subject in combination with any compound conventional for the treatment of GISTs.

In some embodiments, the LIX1 inhibitor of the present invention is administered to the subject in combination with at least one compound selected from the group consisting of Tyrosine kinase inhibitors (TKIs) (such as imatinib and imatinib mesylate), KIT inhibitors, AKT inhibitors (AKTi), sunitinib (sunitinib malate), Regorafenib, chemoradiotherapy, gene therapy and radiotherapy.

In a further aspect, the LIX1 inhibitor of the invention sensitizes GISTs to compounds conventional for the treatment of GISTs such as tyrosine kinase inhibitors.

Accordingly, the present invention relates to the LIX1 inhibitor for use in a method for enhancing therapeutic efficacy of compounds conventional for the treatment of GISTs such as tyrosine kinase inhibitors in a subject in need thereof.

In one embodiment, the present invention relates to the LIX1 inhibitor for use in a method for enhancing therapeutic efficacy of imatinib and imatinib mesylate in a subject in need thereof.

In a further aspect, the present invention relates to a method of screening a candidate compound for use as a drug for treating GISTs in a subject in need thereof, wherein the method comprises the steps of:
  providing a LIX1, providing a cell, tissue sample or organism expressing a LIX1,
  providing a candidate compound such as a small organic molecule, an oligonucleotide, a ribozyme a polypeptide, an aptamer, or an intra-antibody,
  measuring the LIX1 activity,
  and selecting positively candidate compounds that inhibit LIX1 activity.

Methods for measuring LIX1 activity are well known such as described in the Example. For example, measuring the LIX1 activity involves determining a Ki on the LIX1 cloned and transfected in a stable manner into a CHO cell line or human GIST cell line, measuring SMC determination, measuring SMC differentiation, measuring SMC proliferation, and measuring YAP1 expression in the present or absence of the candidate compound.

Tests and assays for screening and determining whether a candidate compound is a LIX1 inhibitor are well known in the art such as described in the Example. In vitro and in vivo assays may be used to assess the potency and selectivity of the candidate compounds to inhibit LIX1 activity.

Activities of the candidate compounds, their ability to bind LIX1 and their ability to inhibit LIX1 activity may be tested using isolated SMC or CHO cell line cloned and transfected in a stable manner by the human LIX1.

Activities of the candidate compounds and their ability to bind to the LIX1 may be assessed by the determination of a Ki on the LIX1 cloned and transfected in a stable manner into a CHO cell line, measuring SMC determination, measuring SMC differentiation, measuring SMC proliferation, and measuring YAP1 expression and transcriptional activity in the present or absence of the candidate compound. The ability of the candidate compounds to inhibit LIX1 activity may be assessed by measuring SMC differentiation and proliferation such as described in the Example.

Cells expressing another RNA-Binding Protein than LIX1 may be used to assess selectivity of the candidate compounds.

Pharmaceutical Composition

The inhibitors of the invention may be used or prepared in a pharmaceutical composition.

In one embodiment, the invention relates to a pharmaceutical composition comprising the inhibitor of the invention and a pharmaceutical acceptable carrier for use in the treatment of gastrointestinal stromal tumors (GISTs) in a subject of need thereof.

Typically, the inhibitor of the invention may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, intramuscular, intravenous, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, intraperitoneal, intramuscular, intravenous and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active inhibitors in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

Pharmaceutical compositions of the invention may include any further compound which is used in the treatment of gastrointestinal stromal tumors (GISTs).

In one embodiment, said additional active compounds may be contained in the same composition or administrated separately.

In another embodiment, the pharmaceutical composition of the invention relates to combined preparation for simultaneous, separate or sequential use in the treatment of gastrointestinal stromal tumors (GISTs) in a subject in need thereof.

The invention also provides kits comprising the inhibitor of the invention. Kits containing the inhibitor of the invention find use in therapeutic methods.

Diagnostic Method

A further aspect of the invention relates to a method of identifying a subject having or at risk of having or developing gastrointestinal stromal tumors (GISTs), comprising a step of measuring in a biological sample obtained from said subject the expression level of LIX1.

The term "biological sample" refers to any biological sample derived from the subject such as blood sample, plasma sample, serum sample or GISTs biopsy sample.

The method of the invention may further comprise a step consisting of comparing the expression level of LIX1 in the biological sample with a reference value, wherein detecting differential in the expression level of LIX1 between the biological sample and the reference value is indicative of subject having or at risk of having or developing gastrointestinal stromal tumors (GISTs).

As used herein, the "reference value" refers to a threshold value or a cut-off value. The setting of a single "reference value" thus allows discrimination between a poor and a good prognosis with respect to the overall survival (OS) for a subject. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. Preferably, the person skilled in the art may compare the expression level (obtained according to the method of the invention) with a defined threshold value. In one embodiment of the present invention, the threshold value is derived from the expression level (or ratio, or score) determined in a biological sample derived from one or more subjects having gastrointestinal stromal tumors (GISTs). Furthermore, retrospective measurement of the expression level (or ratio, or scores) in properly banked historical subject samples may be used in establishing these threshold values.

In one embodiment, the reference value may correspond to the expression level of LIX1 determined in a biological sample associated with a subject not afflicted with gastrointestinal stromal tumors (GISTs). Accordingly, a higher expression level of LIX1 than the reference value is indicative of a subject having or at risk of having or developing gastrointestinal stromal tumors (GISTs), and a lower or equal expression level of LIX1 than the reference value is indicative of a subject not having or not at risk of having or developing gastrointestinal stromal tumors (GISTs).

In another embodiment, the reference value may correspond to the expression level of LIX1 determined in a biological sample associated with a subject afflicted with gastrointestinal stromal tumors (GISTs). Accordingly, a higher or equal expression level of LIX1 than the reference value is indicative of a subject having or at risk of having or developing gastrointestinal stromal tumors (GISTs), and a lower expression level of LIX1 than the reference value is indicative of a subject not having or not at risk of having or developing gastrointestinal stromal tumors (GISTs).

Analyzing the LIX1 expression level may be assessed by any of a wide variety of well-known methods for detecting expression of a transcribed nucleic acid or translated protein.

In one embodiment, the LIX1 expression level is assessed by analyzing the expression of mRNA transcript or mRNA precursors, such as nascent RNA, of LIX1 gene. Said analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TaqMan), and probes arrays such as GeneChip(™) DNA Arrays (AFFYMETRIX).

Advantageously, the analysis of the expression level of mRNA transcribed from the gene encoding for LIX1 involves the process of nucleic acid amplification, e.g., by RT-PCR (the experimental embodiment set forth in U.S. Pat. No. 4,683,202), ligase chain reaction (Barany, 1991), self sustained sequence replication (Guatelli et al., 1990), transcriptional amplification system (Kwoh et al., 1989), Q-Beta Replicase (Lizardi et al., 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another embodiment, the LIX1 expression level is assessed by analyzing the expression of the protein translated from said gene. Said analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the protein translated from the gene encoding for LIX1.

Said analysis can be assessed by a variety of techniques well known from one of skill in the art including, but not limited to In Situ Hybridization, immunofluorescence Staining, enzyme immunoassay (EIA), radioimmunoassay (RIA), Western blot analysis and enzyme linked immunoabsorbant assay (RIA).

In a further aspect, the present invention relates to a method of determining whether the gastrointestinal stromal tumor (GIST) of a subject is a low risk tumor or a high risk tumor, comprising the steps of:

(i) measuring in a biological sample obtained from said subject the expression level of LIX1, (ii) comparing the LIX1 expression level in the biological sample with a reference value, (iii) detecting differential in the LIX1 expression level between the biological sample and the reference value is indicative that the gastrointestinal stromal tumor (GIST) is a low risk tumor or a high risk tumor.

The term "low risk GISTs" or "low risk tumor" has its general meaning in the art and refers to GISTs or tumor with low risk of clinically aggressive behavior. The term "low risk GISTs" refers to GISTs in a subject with low relapse risk. The term "low risk GISTs" also refers to GISTs in a subject with high relapse-free overall survival. The term "low risk GISTs" also refers to GISTs in a subject with high overall survival.

The term "high risk GISTs" or "high risk tumor" has its general meaning in the art and refers to GISTs or tumor with high risk of clinically aggressive behavior. The term "high risk GISTs" refers to GISTs in a subject with high relapse risk. The term "high risk GISTs" also refers to GISTs in a subject with reduced relapse-free overall survival. The term "high risk GISTs" also refers to GISTs in a subject with reduced overall survival.

According to the invention, a lower LIX1 expression level in the biological sample than the reference value is indicative that the gastrointestinal stromal tumor (GIST) is a low risk tumor and higher LIX1 expression level in the biological sample than the reference value is indicative that the gastrointestinal stromal tumor (GIST) is a high risk tumor.

In a further aspect, the present invention relates to a LIX1 inhibitor for use in the prevention of progression of low risk gastrointestinal stromal tumors (GISTs) to high risk gastrointestinal stromal tumors (GISTs) in a subject in need thereof wherein the subject was being classified as having a high risk tumor by the method as above described.

The method of the invention is particularly suitable for determining the relapse-free overall survival or the overall survival (OS) of a subject afflicted with gastrointestinal stromal tumors (GISTs).

Accordingly, the present invention relates to a method for predicting the survival time of a subject afflicted with gastrointestinal stromal tumors (GISTs) comprising the steps of:

(i) measuring in a biological sample obtained from said subject the expression level of LIX1, (ii) comparing the LIX1 expression level in the biological sample with a reference value, and iii) providing a good prognosis when the LIX1 expression level is lower than the predetermined reference value, and a poor prognosis when the LIX1 expression level is higher than the predetermined reference value.

A further aspect of the invention relates to a method of monitoring gastrointestinal stromal tumors (GISTs) progression by performing the method of the invention.

In one embodiment, the present invention relates to a method of treating gastrointestinal stromal tumors (GISTs) in a subject in need thereof comprising the steps of:

(i) identifying a subject having or at risk of having or developing a gastrointestinal stromal tumors (GISTs) by performing the method according to the invention, and (ii) administering to said subject a LIX1 inhibitor when it is concluded that the subject has or is at risk of having gastrointestinal stromal tumors (GISTs).

In one embodiment, the present invention relates to a method of preventing the progression of low risk gastrointestinal stromal tumors (GISTs) to high risk gastrointestinal stromal tumors (GISTs) in a subject in need thereof comprising the steps of:

i) determining whether the gastrointestinal stromal tumor (GIST) of a subject is a low risk tumor or a high risk tumor by performing the method according to the invention, and ii) administering a LIX1 inhibitor if said subject was being classified as having a high risk tumor.

The invention will be further illustrated by the following figures and examples. However, these examples and figures should not be interpreted in any way as limiting the scope of the present invention.

FIGURES

FIG. 1: LIX1 is expressed in GISTs. (A) LIX1 mRNA expression and regulation in the GIST882 cell line. (a) Semi-quantitative RT-PCR analysis of LIX1 transcript level in 131N1 (astrocytoma cells), PC3 (prostate cancer cells), HeLa, and GIST882 cells. Loading was verified by glyceraldehyde-3-phosphate dehydrogenase (GAPDH) expression. (b) Analysis of LIX1 expression by RT-qPCR in GIST882 cells upon incubation with DMSO alone (control) or with 7.5 µM of Akti (inhibitor of AKT) for 6 h, 24 h and 48 h. Normalized expression levels were converted to fold changes. *P<0.05; **P<0.01. (c) Analysis of LIX1 expression by RT-qPCR in GIST882 cells upon incubation with DMSO alone (control) or with 1 µM of imatinib mesylate (KIT inhibitor) for 6 h, 24 h and 48 h. Normalized expression levels were converted to fold changes. *P<0.05; P<0.01; *P<0.001. (B) (a) Analysis of the correlation between LIX1 expression level and relapse rates. (b) Relapse-free survival from initial imatinib mesylate treatment in group 1 presenting low level of LIX1 compared with group 2 presenting high level of LIX1 individuals with GIST, assessed in a univariate analysis using the Kaplan-Meier method. The log-rank test was used. SubM, submucosa; CSM, circular smooth muscle; LSM, longitudinal smooth muscle.

Figure 2:
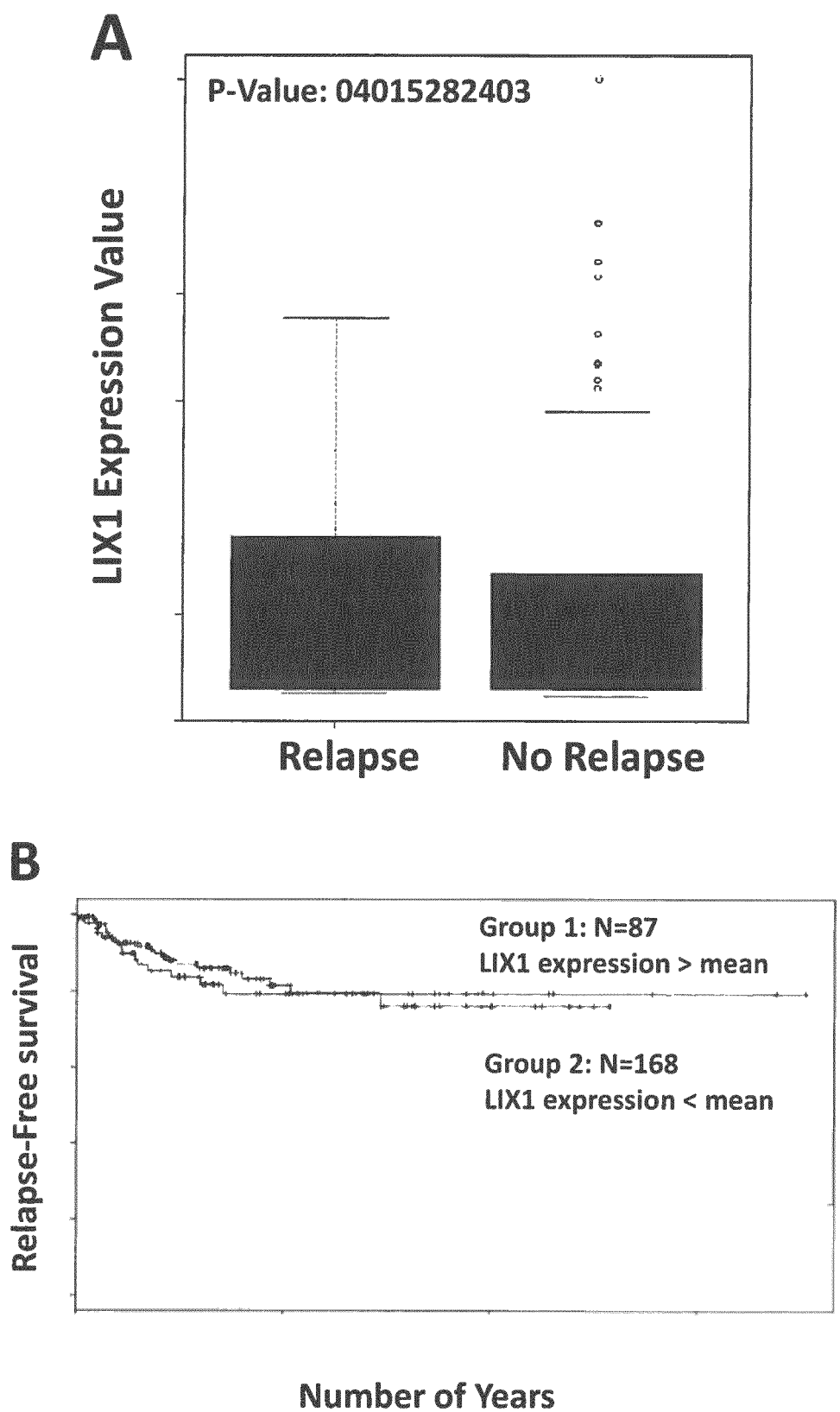

FIG. 2: High LIX1 expression is not associated with poor patient prognosis in non-GIST sarcomas. (A) Correlation between LIX1 expression level in primary sarcomas with or without relapse after treatment. (B) Relapse-free post-treatment survival in group 1 presenting low level of LIX1 (n=168) compared with group 2 presenting high level of LIX1 (n=87) individuals with sarcomas, assessed in univariate analysis using the Kaplan-Meier method. The log-rank test was used.

Figure 3:
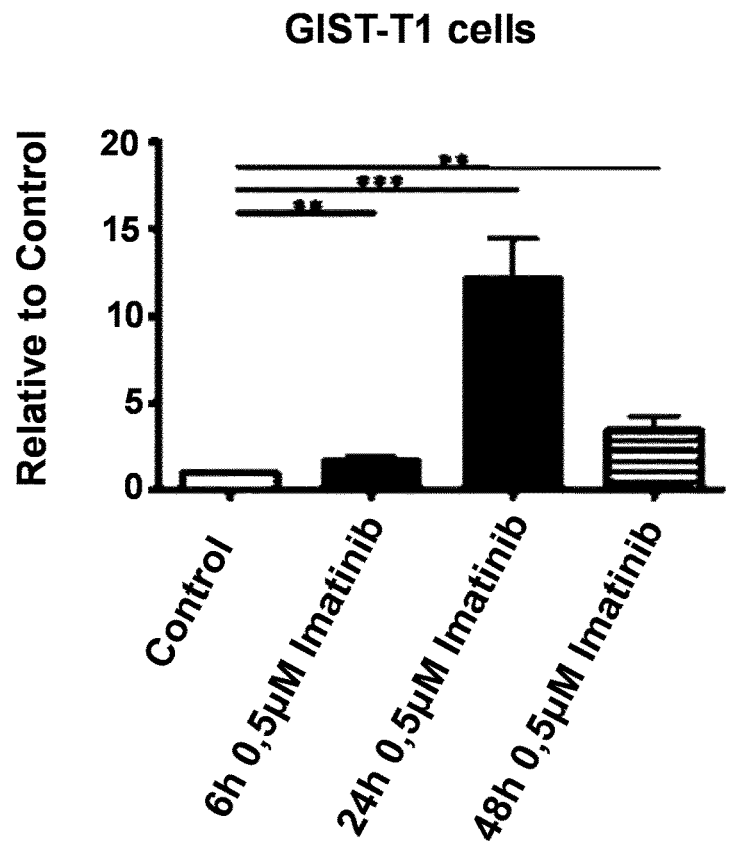

FIG. 3: LIX1 is upregulated by Imatinib treatment in GIST-T1 cell line. Analysis of LIX1 expression by RT-qPCR in GIST-T1 cells upon incubation with DMSO alone (control) or with 0.5 µM of imatinib mesylate (KIT inhibitor) for 6 h, 24 h and 48 h. Normalized expression levels were converted to fold changes. $P<0.01$; *$P<0.001$.

Figure 4:
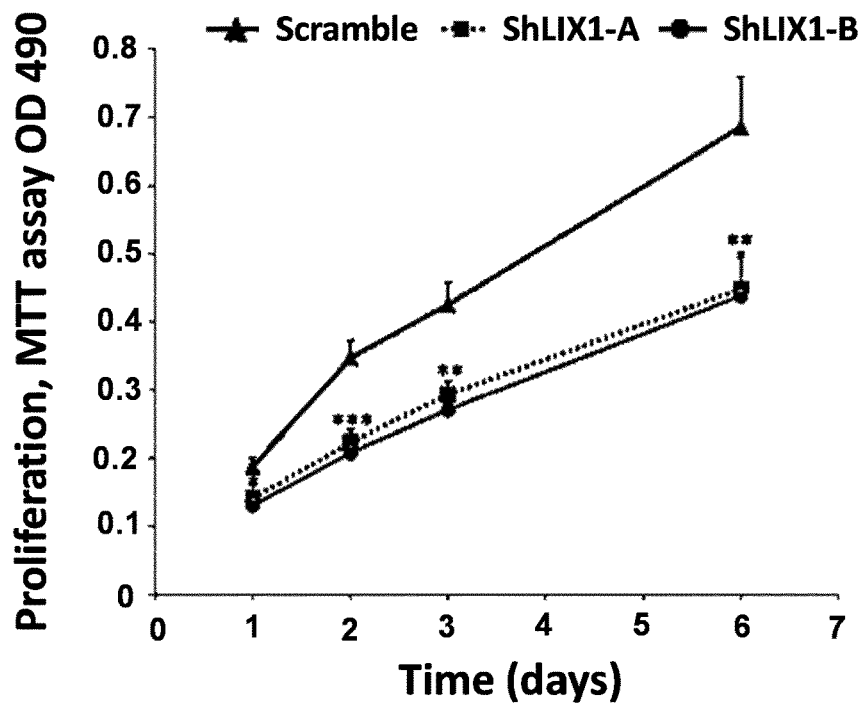

FIG. 4: Downregulation of LIX1 decreases GIST cell proliferation in vitro. GIST-T1 proliferation on ShScramble, ShLIX1-A and ShLIX1-B GIST-T1 cell line were obtained using MTT assays (MTT: 3-(4,5-dimethylthiazol-2-yl)-2,5-diphenyltetrazolium bromide). Statistical analyses for 6 days of three independent experiments in the presence of mitomycin C (*$P<0.001$; $P<0.01$).

Figure 5:
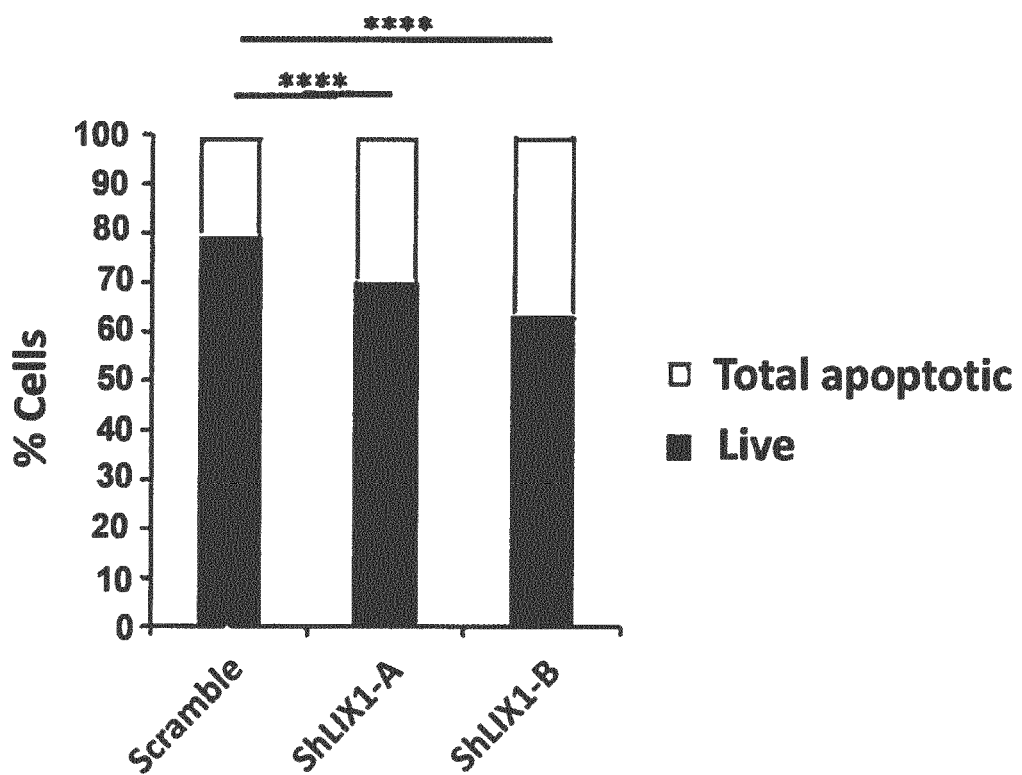

FIG. 5: Downregulation of LIX1 increases GIST cell apoptosis in vitro. GIST-T1 apoptosis on ShScramble, ShLIX1-A and ShLIX1-B GIST-T1 cell line were obtained using Muse Annexin V & Dead Cell Assay. Statistical analyses of three independent experiments in the presence of mitomycin C (****$P<0.0001$).

Figure 6:
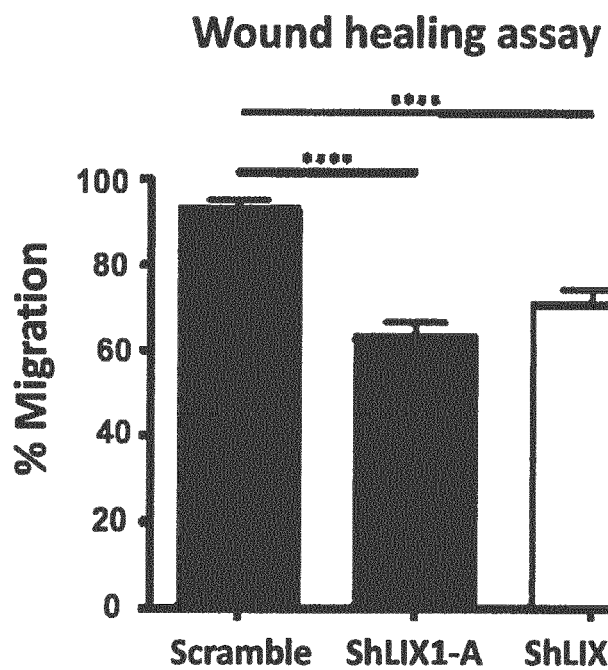

FIG. 6: Downregulation of LIX1 decreases GIST cell migration in vitro. Statistical analyses of wound-healing assays on ShScramble, ShLIX1-A and ShLIX1-B GIST-T1 cell line. Results of three independent experiments in the presence of mitomycin C (***$P<0.001$).

Figure 7:
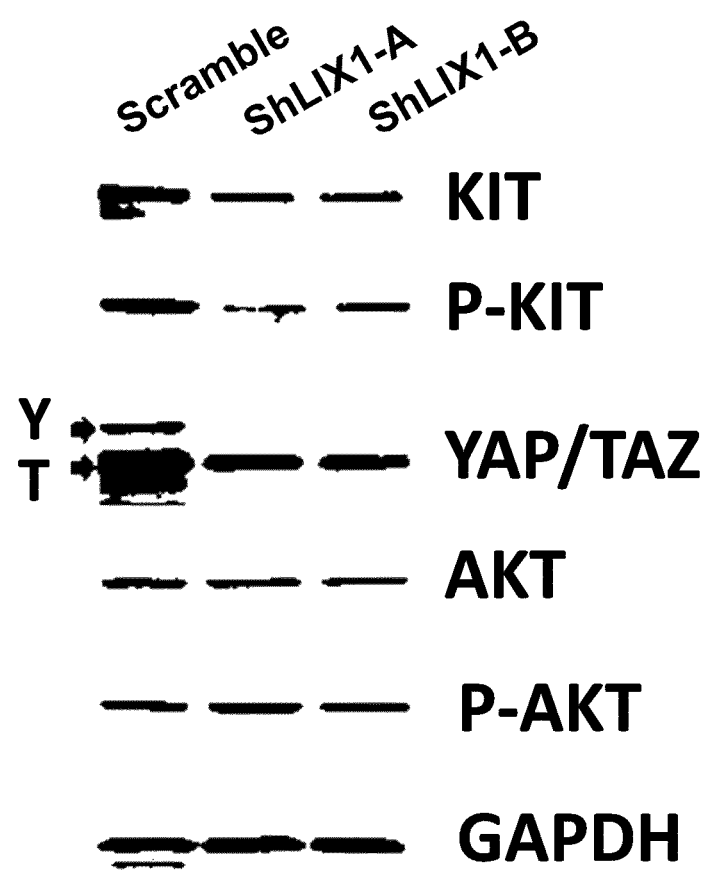

FIG. 7: Downregulation of LIX1 decreases KIT and YAP/TAZ expression and activities. Representative western blot analysis of KIT, YAP/TAZ, AKT or KIT and AKT phosphorylation in extracts from ShScramble, ShLIX1-A and ShLIX1-B GIST-T1 cell line compare to loading control (GAPDH).

EXAMPLES

Example 1

LIX1 Regulates YAP1 Activity and Controls the Proliferation and Differentiation of Stomach Mesenchymal Progenitors Material & Methods
Chick Embryonic GI Tissues Fertilized White Leghorn eggs from the Haas Farm (France) were incubated at 38° C. in humidified incubators. Embryos were staged according to Hamburger and Hamilton (1951) [44]. Isolation of mesodermal and endodermal layers from stage 25 stomachs (referred to as E5) was performed as previously described [8]. The efficiency of dissections was evaluated by monitoring the expression of SHH and BARX1, which are specific markers of the epithelial and mesenchymal layers respectively.

Avian Retroviral Misexpression System and Constructs

Chick LIX1 full-length cDNA was isolated from total mRNA extracts of E5 stomachs. The mouse YAP1, the chick full-length LIX1, the human full-length LIX1 and the Short hairpin RNA of LIX1 (ShLIX1) associated with the mouse U6 promoter were cloned into the shuttle vector Slax13 and then subcloned into the Replication-Competent Avian Leucosis Sarcoma virus strain A (RCAS(A)) or strain B (RCAS (B)) vectors. FGF8, sFGFR2b, and GFP retroviral constructs have been previously described [8]. RCAS-shPROX1 retrovirus [45] served as unrelated RCAS-ShRNA retroviruses. Retroviral constructs were transfected into the chicken DF-1 fibroblast cell line (ATCC-LGC) to produce retroviruses. Retroviruses were titered using standard techniques and injected into the splanchnopleural mesoderm of E1.5 chicken embryos to target the stomach mesenchyme [22]. Embryos were co-injected with RCAS-GFP to allow screening of correctly targeted stomachs. Eggs were then placed at 38° C. until harvested. Efficient retroviral infection was confirmed by in situ hybridization analysis on paraffin sections using ENV probes, or, in LIX1 misexpression experiments only, LIX1 probes. Infection with RCAS-GFP retroviruses does not affect chick stomach development. Stomach phenotypes from infected embryos were analysed by comparison with uninfected control embryos incubated at the same time.

Cell Cultures and Analysis

The chicken DF-1 fibroblast cell line was cultured as previously described [22]. Cell growth in DF-1 cultures was assessed using the Muse Count and Viability reagent following the manufacturer's specifications (Muse Cell Analyzer-Millipore). DF-1 cells were plated on plastic at 2000 cells/cm$^2$ to obtain low-density cultures and 6000 cells/cm$^2$ to obtain high-density cultures. Verteporfin (Sellekchem) was used applied to DF-1 cells for 20 hours at a final concentration of 1 µM.

In Situ Hybridization and Immunofluorescence Staining

Dissected GI tissues were fixed in 4% paraformaldehyde at room temperature for 30 minutes, washed in PBS, gradually dehydrated in methanol and stored at −20° C. before processing for whole-mount in situ hybridization as previously described [8,22]. For sections, GI tissues were fixed in 4% paraformaldehyde at room temperature for 30 minutes, washed in PBS, gradually dehydrated in ethanol and embedded in paraffin. 10-µm sections were cut using a microtome and collected on poly-L-lysine-coated slides (Thermo Fisher). Partial chick YAP1, CTGF, CYR61 cDNAs were isolated from total mRNA extracts of E5 stomachs. In situ hybridization experiments on whole-mount and paraffin sections were carried out as previously described [24] using chick LIX1 and YAP1 probes and published SM22, BAPX1, SOX10 and ENV probes [8,19,24]. Immunofluorescence studies were performed on paraffin sections using polyclonal antibodies against αSMA (Sigma, 1:400 dilution), anti-Phospho-Histone H3-Ser10 (PH3) (Millipore, 1:300 dilution) and cleaved CASPASE-3 (5A1E, Cell Signaling, 1:400 dilution), and monoclonal antibodies against CALPONIN (Sigma, 1:500 dilution). Nuclei were labelled with Hoechst (Invitrogen). In vivo proliferation rates were assessed by counting the number of PH3-positive cells relative to the total number of nuclei in the section. Cell density was assessed on images of stomach sections by calculating the area occupied by Hoechst-stained nuclei relative to the total area of the section.

Reverse Transcription and Quantitative Polymerase Chain Reaction (RT-qPCR)

Total RNA was extracted from stomachs or cell cultures with the HighPure RNA Isolation kit (Roche). Reverse transcription was performed using the Verso cDNA synthesis kit (Thermo Scientific) and RT-qPCR was performed using LightCycler technology (Roche Diagnostics). PCR primers were designed using the LightCycler Probe Design 2.0 software. Each sample was analysed in three independent experiments done in triplicate. Expression levels were determined with the LightCycler analysis software (version 3.5) relative to standard curves. Data were represented as the mean level of gene expression relative to the expression of the reference genes UBIQUITIN or GAPDH. Relative mRNA expression was calculated using the $2^{-\Delta\Delta C_T}$ method.

Western Blotting

DF-1 cells and chick stomachs were re-suspended in lysis buffer (20 mM Tris pH8, 50 mM NaCl, 1% NP40, cOmplete EDTA-free Protease Inhibitor Cocktail (Roche)). 10 µg of total protein lysates were boiled in SDS-PAGE sample buffer, separated by 10% SDS-PAGE and transferred to nitrocellulose membranes. Membranes probed with rabbit anti-phospho-YAP (Ser127) (4911, Cell Signaling, 1:1000 dilution), anti-YAP/TAZ (8418, Cell Signaling, 1:1000 dilution), or anti-GAPDH (Sigma, 1:5000 dilution) antibodies overnight. Glyceraldehyde-3-phosphate dehydrogenase (GAPDH) expression was used to confirm equal loading. All immunoblots were developed and quantified using the Odyssey infrared imaging system (LICOR Biosystems) and infrared-labeled secondary antibodies.

Statistical Analysis

Data were analysed by performing two-tailed, or, when appropriate, one-tailed Mann-Whitney tests using GraphPad Prism 6 software. Results were considered significant when P<0.05 (*), P<0.01 (), P<0.001 (*) or P<0.0001 (****).

Photography

Images were acquired using a Nikon Multizoom AZ100 stereomicroscope and a Carl Zeiss Axiolmager microscope.

Results

LIX1 Defines Stomach Mesenchymal Progenitors

We previously screened for genes that demonstrated higher expression at the earliest stages of stomach development [8] and found LIX1 to be among them. Real-time quantitative PCR (RT-qPCR) analyses on stomach extracts confirmed the dynamic and transitory nature of LIX1 expression during stomach development. While high levels of LIX1 transcripts were detected at embryonic day 4 (E4), levels of LIX1 transcripts quickly decreased with the onset of SMC determination (as visualized through the expression of αSMA and SM22), to finally barely detectable levels at E7, when SMC differentiation occurred (as shown by the high level of CALPONIN and CALDESMON expression). In parallel, we monitored the levels of BARX1, a marker of stomach mesenchyme [19], as well as SRF and its co-activator MYOCARDIN, which control SMC differentiation [20,21], and found that these genes were detected throughout all examined stages. These results suggest that LIX1 is an early marker of stomach development. We further studied the precise expression pattern of LIX1 in the developing GI tract by in situ hybridization analysis. Strong LIX1 expression was detected at E4 throughout the stomach mesenchyme and levels quickly decreased from E5 onwards. LIX1 transcripts were mainly detected in the pylorus at E5 and in the most posterior part of the stomach at E6. When comparing the dynamics of LIX1 expression in the developing stomach with the kinetics of αSMA, the early marker of SMC determination in adjacent stomach sections, we observed that their expression domains appeared mutually exclusive. While LIX1 expression was high in stomach mesenchymal progenitors, it progressively decreased with the onset of SMC determination, thus identifying LIX1 as a novel and unique stomach marker, restricted to mesenchymal progenitors.

LIX1 Silencing Impairs Mesenchyme Determination and Decreases YAP1 Activity

The complementarity between LIX1 and αSMA expression prompted us to investigate whether LIX1 is required for the process of stomach SMC determination. This was accomplished using the avian replication-competent retroviral (RCAS) transgenesis method that allows in vivo gain- or loss-of-function approaches of specific genes in the stomach mesenchyme [6,8,19,22]. We first performed LIX1 loss-of-function experiments using RCAS-ShLIX1 (short-hairpin RNA directed against LIX1) retroviruses. When injected into the presumptive domain of the developing stomach, RCAS-ShLIX1 retroviruses led to a specific decrease in endogenous LIX1 expression, demonstrated by in situ hybridization and RT-qPCR analyses. LIX1 silencing induced a decrease in the expression of the SMC determination markers αSMA and SM22 in E6.5 ShLIX1-expressing stomachs compared to controls. In contrast, injection of unrelated RCAS-ShRNA retroviruses, which do not target LIX1, had no effect on αSMA expression. Moreover, when RCAS-ShLIX1 retroviruses were co-injected with RCAS-hLIX1 retroviruses, which induce the expression of the human LIX1 protein insensitive to the chick-specific RCAS-ShLIX1 retroviruses, normal expression of αSMA was restored, demonstrating the specificity of the ShLIX1 construct for LIX1. Levels of BARX1 transcripts were comparable in ShLIX1-expressing stomachs compared to controls, indicating that the patterning of the stomach was unaffected by LIX1 silencing. We also observed a decrease in MYOCARDIN expression, while levels of SRF transcripts were not significantly affected in E6.5 ShLIX1-expressing stomachs compared to controls. In addition, we found that LIX1 silencing induced a smaller determined-SMC territory, as demonstrated by in situ hybridization and immunostaining analyses on ShLIX1-expressing stomach sections compared to controls. The diminished expression of αSMA and SM22 was associated with a 40% decrease in the rate of cell proliferation in ShLIX1-expressing stomach sections compared to controls, as demonstrated by immunostaining analysis for phosphorylated histone 3-Ser10 (PH3), a standard marker of the G2/M transition [6]. These results are in line with a role for LIX1 in regulating cell proliferation, as previously shown in studies on cricket (*Gryllus bimaculatus*) and mouse that identified homologs of LIX1 as positive regulators of cell proliferation [10,18]. Lowfat, the arthropod homolog of LIX1 has been characterized, through its interaction with the atypical cadherins fat and dachsous, as a component of the Hippo pathway [10,12]. As the key downstream regulator of the Hippo pathway is the pro-proliferative gene Yes-Associated Protein (YAP1), we next investigated whether LIX1 regulates the expression of YAP1 during this process. In situ hybridization and RT-qPCR analyses revealed that endogenous transcripts of YAP1 and its transcriptional targets CTGF and CYR61, known to stimulate cell proliferation [15,23], are abundant during early development of the stomach (E4-E5.5). At this stage, their expression is detectable in both the mesenchymal and epithelial layers of the stomach, as demonstrated by RT-qPCR analyses on layer-dissociated stomach extracts. RT-qPCR analysis showed a reduction in the level of YAP1 transcripts and YAP1 activity, monitored through the expression of CTGF and CYR61, in ShLIX1-expressing stomachs compared to controls. Moreover, LIX1 silencing also induced a decrease in the expression of TEAD transcription factors (TEAD1 and TEAD4). Taken together, our results show that when LIX1 expression was silenced in the developing stomach, SMC determination was hindered. This was associated with a decrease in cell proliferation and a decrease in YAP1 transcript levels and YAP1 activity in the developing mesenchyme. Our finding highlights the requirement of LIX1 expression in the stomach mesenchymal progenitors to establish normal proliferation rates and allow proper SMC determination.

LIX1 Misexpression Expands the Determined SMC Domain and Stimulates Cell Proliferation and YAP1 Activity We next induced a misexpression of LIX1 in the stomach mesenchyme using RCAS-LIX1 retroviruses. This did not drastically affect GI morphogenesis, as the morphology of LIX1-misexpressing stomachs resembled that of control embryos. We first observed a premature expression of SMC determination marker SM22 as early as E4.5 in LIX1-misexpressing stomachs, whereas SMC determination had not yet taken place in controls, suggesting that LIX1 misexpression facilitated SMC determination. As a result, we observed at E6 that LIX1-misexpressing stomachs harboured an expanded determined SMC territory at the expense of the adjacent domains, mainly the intermuscular tendons and the submucosa. This was demonstrated both by whole-mount in situ hybridization, which showed a larger expression domain of determined SMC markers SM22 and BAPX1 [24] in LIX1-misexpressing stomachs compared to controls, and by αSMA immunostaining on sections showing that sustained LIX1 expression led to a decrease in the size of the submucosa. Accordingly, analysis of the enteric nervous system (ENS) network using in situ hybridization of SOX10 transcripts revealed that ENS precursors, which normally colonize the SMC domain specifically [8], had migrated into the adjacent tendon territory, further indicating an expanded SMC domain in LIX1-misexpressing stomachs compared to controls. Further analysis by RT-qPCR demonstrated that, compared to control stomachs, LIX1-misexpressing stomachs harboured higher levels of αSMA, BARX1 and SRF transcripts at E6, whereas MYOCARDIN levels were slightly reduced. Taken together, our in vivo results indicate that LIX1 is not only necessary for correct SMC determination, but that it also acts in favour of the process. These changes are associated with an increase in the rate of cell proliferation, as demonstrated by immunostaining analysis for PH3, and consequently to an increase in mesenchymal cell density in E6 LIX1-misexpressing stomachs compared to controls. The rate of cell death, however, was comparable in both conditions, as demonstrated by immunostaining analysis of cleaved CASPASE-3. Moreover, RT-qPCR analysis indicated an increase in the expression of pro-proliferative genes YAP1, CTGF, CYR61, TEAD1 and TEAD4 in LIX1-misexpressing stomachs compared to controls.

The differences in YAP1 expression and activity that we observed in LIX1-misexpressing stomachs could be linked to the changes in the identity of the tissue associated with aberrant LIX1 expression, or could be due to a role of YAP1 as a key relay in the establishment of the LIX1 phenotype. We thus performed YAP1 gain-of-function experiments in the developing stomach using RCAS-YAP1 retroviruses. While YAP1 misexpression did not affect the endogenous expression of LIX1 (data not shown), higher expression levels of αSMA and MYOCARDIN transcripts were observed at E6, while levels of BARX1, SRF, TEAD1 and TEAD4 were not significantly affected. Moreover, we observed an expanded SM22-positive determined SMC domain in YAP1-misexpressing stomachs compared to control stomachs. These changes were associated with an increase in cell proliferation, as demonstrated by immunostaining analysis for PH3. Our results thus demonstrate that LIX1 stimulates the endogenous level of YAP1 transcripts and YAP1 activity and that sustained YAP1 activity phenocopies LIX1 misexpression regarding stomach mesenchyme determination. Furthermore, when RCAS-ShLIX1 retroviruses were co-injected with RCAS-YAP1 retroviruses, the expression of LIX1 was not rescued. However, the restored YAP1 activity (monitored through the expression of CYR61 and CTGF transcripts) rescued the expression of αSMA. Altogether, these data demonstrate that YAP1 is a key relay in the establishment of the LIX1 phenotype.

Endogenous LIX1 Expression is Regulated by the FGF Pathway During SMC Determination Collectively, our in vivo loss- and gain-of-function experiments demonstrate that LIX1 expression must be finely regulated in the stomach mesenchyme to control the pool of progenitors required for correct SMC determination, presumably through the regulation of YAP1 activity. It has been shown that aberrant activation of the FGF pathway has a negative impact on stomach SMC determination [8]. As we report that LIX1 silencing impaired SMC determination, we next investigated whether the FGF signalling pathway could downregulate LIX1 expression. To address this question, we activated the FGF signalling pathway by misexpressing FGF8 in the stomach mesenchyme using RCAS-FGF8 retroviruses and confirmed that this led to hindered mesenchyme determination, as demonstrated by RT-qPCR experiments showing lower levels of αSMA and SM22 transcripts in FGF8-misexpressing stomachs compared to controls. The upregulation of FGF activity was associated with a strong decrease in LIX1 transcript levels compared to control stomachs, which was monitored by RT-qPCR experiments and in situ hybridization analysis. Additionally, FGF8 misexpression decreased the levels of YAP1 transcripts. These results suggest that sustained FGF activity during SMC determination phenocopies LIX1 loss-of-function. Conversely, when using RCAS-sFGFR2b retroviruses, which produce a secreted form of FGFR2b [8,25], we found that inhibition of FGF pathway activity induced an increase in LIX1 levels at E6.5 compared to control stomachs. Taken together, these results suggest that the FGF pathway regulates the endogenous expression of LIX1 and thereby maintains the proper levels necessary to ensure correct stomach mesenchyme determination.

Sustained LIX1 Expression Decreases YAP1 Activity and Hinders SMC Differentiation To further understand the role of LIX1 in the development of the stomach mesenchyme, we next analysed the consequences of LIX1 misexpression on SMC differentiation, the later step of SMC development. We found that differentiation was impaired in LIX1-misexpressing stomachs, as demonstrated at E7 both by the reduction of CALPONIN immunostaining on stomach sections and the reduction of CALPONIN transcript levels analysed by RT-qPCR. We also observed a decrease in the expression of MYOCARDIN, while levels of BARX1 and SRF transcripts were not significantly affected. The decrease in CALPONIN and CALDESMON transcript expression in LIX1-misexpressing stomachs was also observed later in development at E8.5, suggesting that the reduced level of differentiation markers did not simply reflect a delay in stomach SMC development. We found that YAP1 misexpression also hindered CALPONIN expression, as demonstrated by immunostaining on stomach sections and by RT-qPCR analysis. These results suggest that while LIX1 misexpression and YAP1 stimulation had a positive impact on SMC determination, they hindered SMC differentiation. Surprisingly, we found that when LIX1 expression was sustained in the developing stomach, the downregulation in the expression of SMC differentiation markers was associated with a lower rate of proliferation. Indeed, mesenchymal cell density was comparable in LIX1-misexpressing stomach compared to controls. It has been shown that the Hippo pathway acts as a sensor of cell density [16,17], thus mediating the relationship between cell proliferation and cell contact inhibition of proliferation. As cell density becomes higher, the Hippo pathway is activated, resulting in an inhibitory phosphorylation of YAP1 and thus a decrease in cell proliferation [26]. Interestingly, RT-qPCR analysis revealed lower transcript levels of TEAR', TEAD4 and YAP1 pro-proliferation targets CYR61 and CTGF in YAP1-misexpressing stomachs compared to controls. The decrease in YAP1 activity in YAP1-misexpressing stomachs at E7 was further confirmed by western blot analysis showing an increase of the inactive phosphorylated form of YAP1 compared to controls. These results indicate that while YAP1 misexpression in the stomach stimulated YAP1 transcriptional activity at determination stages, a decrease in YAP1 activity was observed later on at differentiation stages. Our hypothesis is that sustained LIX1 expression led to a decrease in YAP1 activity consecutive to cell contact inhibition of proliferation, as a consequence of the early stimulation of mesenchymal progenitor proliferation, and this could be inhibitory for SMC differentiation. In line with this hypothesis, RT-qPCR analysis revealed lower transcript levels of TEAR', TEAD4 and YAP1 pro-proliferation targets CYR61 and CTGF in LIX1-misexpressing stomachs compared to controls. The decrease in YAP1 activity in LIX1-misexpressing stomachs at E7 was further confirmed by western blot analysis showing an increase of the inactive phosphorylated form of YAP1 compared to controls. These data indicate that Hippo signalling was activated as a result of sustained LIX1 expression at E7. Altogether, our results demonstrate that LIX1 has an early role in the process of stomach SMC determination, through the regulation of YAP1-induced mesenchymal progenitor proliferation. However, as stomach development proceeds, sustained LIX1 expression has a negative impact on further SMC differentiation and this is associated with a decrease in YAP1 activity.

The Ability of LIX1 to Regulate Cell Proliferation is Dependent on Cell Density

These results prompted us to investigate the role of LIX1 in regulating both proliferation and contact inhibition of proliferation in heterologous cell cultures. DF-1 chicken fibroblasts were infected with replication-competent RCAS retroviruses and cultured for 5 days to ensure homogeneous expression. When seeded at low density, after one day in culture, LIX1-expressing cells demonstrated a higher expression of YAP1 transcript and protein levels compared to control cells. This greater expression was associated with higher transcript levels of YAP1 pro-proliferation target genes CTGF and CYR61 and an increase in cell proliferation. Interestingly, when LIX1-expressing cells where treated with verteporfin, an inhibitor of the YAP-TEAD interaction that abrogates YAP activity [27,28], while the upregulation of YAP1 was still observed, levels of CTGF and CYR61 transcripts and rates of proliferation were comparable with control cells. Analysis of cell death in these cultures confirmed that this result was not due to a cytotoxic effect of verteporfin. These data demonstrate that, at low density, LIX1 regulates cell proliferation through modulation of YAP1 activity. After 3 days in culture, LIX1-expressing cells had grown faster than control cells. However, although YAP1 expression in LIX1-expressing cells remained higher than in controls, the levels of CTGF and CYR61 transcripts were similar to control levels. In addition, we observed an increase of the inactive phosphorylated form of YAP1 compared to controls in LIX1-expressing cells, indicating that YAP1 activity was downregulated at Day 3 compared to Day 1. These data suggest that under the influence of LIX1, a compensatory response to growing cell density took place. Indeed, while LIX1 acts to promote cell proliferation at low cell density, its pro-proliferation activity is abolished when cells had grown, suggesting that its ability to regulate cell proliferation is dependent upon cell density. In line with this hypothesis, when cells were seeded at high density, levels of CTGF and CYR61 transcripts, YAP1 activity and rates of proliferation were comparable in controls and LIX1-expressing cells after one day in culture. The overexpression of LIX1 in vitro thus recapitulates the effects we had observed under misexpression of LIX1 in vivo during stomach mesenchyme development, suggesting that LIX1 drives an increase in cell density that feeds back on the system to block the activity of YAP1 and further proliferation.

Discussion

Our study first identified LIX1 as a novel and so far unique marker of stomach mesenchymal progenitors. To our knowledge, LIX1 is the first described gene to define the population of mesenchymal progenitors and to allow discrimination between undetermined and determined SMC states in the stomach. Collectively, our in vivo gain- and loss-of-function experiments clearly demonstrate that LIX1 is a key regulator of stomach mesenchyme development, by regulating both the determination and the differentiation of SMCs. Our study further demonstrates that YAP1 is a key relay of the function of LIX1 during these developmental processes.

We first identified LIX1 as an essential regulator of stomach mesenchyme determination. We thus suspect that the expression of LIX1 must be tightly regulated in the developing mesenchyme to allow fine-tuning of the transcript levels and the state of activation of the pro-proliferative transcriptional coactivator YAP1, which in turn controls the rates of proliferation required for correct SMC determination. We further show that the FGF signalling pathway could be involved in the regulation of LIX1 expression at determination stages. Most of the studies published so far identified some regulators of YAP1 at the level of its activity, through its phosphorylation, localisation and stability [29]. Our study identifies LIX1 as a new regulator of YAP1 at the transcriptional level, which is a novel finding. Interestingly, our functional in vivo data demonstrate that LIX1 regulates not only YAP1 transcripts levels but also those of the TEAD transcription factors TEAD1 and TEAD4, which are essential in mediating YAP-dependent gene expression [15], indicating that LIX1 is an upstream regulator of YAP signalling. Further investigations will allow us to understand by which mechanisms LIX1 regulates the level of YAP1 and TEAD transcripts. Interestingly, in silico studies have shown that LIX1 has a double-stranded RNA-binding domain, suggesting that it could be involved in mRNA or microRNA processing [10] and it has been shown that miR-506 and miR-375 regulate YAP1 expression [30,31]. It would thus be interesting to study whether LIX1 has a direct impact on YAP1 TEAD mRNA expression and/or stability.

We then demonstrated that LIX1 is an essential regulator of SMC differentiation. Intriguingly, while the pro-proliferative activity of LIX1 presumably facilitates SMC determination, LIX1 has a negative impact on further SMC differentiation. We suspect that high proliferative activity of LIX1 led to cell contact inhibition of proliferation, revealing the presence of a negative feedback loop on the endogenous expression and activity of YAP1 within the stomach mesenchyme to compensate for aberrant cell proliferation. Accordingly, we never observed hypertrophic stomachs under LIX1 influence, suggesting that LIX1 pro-proliferation activity is limited by the overall size of the stomach. In response to high cell density, the Hippo pathway regulates YAP1 activity through inhibitory phosphorylation [32] and we report here that the defect in SMC differentiation is associated with an increase in phosphorylated YAP1 in LIX1-misexpressing stomachs. While the Hippo pathway has already been investigated in the context of gastrointestinal epithelia [28, 29, 30, 33], our study is the first to suggest a role for this pathway in regulating the proliferation and differentiation of the gastrointestinal mesenchyme. Along these lines, the next step would be to address the possible regulation of the Hippo pathway by LIX1 in this developmental process. Lowfat, the arthropod homolog of LIX1, interacts with the atypical cadherins fat and dachsous and stabilizes FAT protein levels [12]. Although a recent study has shown that the vertebrate ortholog of FAT does not seem to regulate the Hippo pathway [34], FAT signalling has been shown to decrease YAP1 activity [35,36]. One could thus speculate that in the context of cell contact inhibition of proliferation, LIX1 participates more directly in the inhibition of YAP1 through the stabilization of FAT levels. Further investigations should focus on uncovering the potential molecular links that tie LIX1 to the regulation of YAP1 phosphorylation and transcriptional output.

Similarly to our conclusions for LIX1, we also report that while the pro-proliferative activity of YAP1 presumably facilitates SMC determination, it is sensitive to cell contact inhibition of proliferation and has a negative impact on further SMC differentiation. Because our misexpression experiments only led to mild overexpression of YAP1 (ranging from 1.2- to 3-fold), we speculate that the native stomach mesenchyme is poised to respond to mild over-activity of YAP1 by turning on the negative feedback loop on YAP1 activity. This finding contrasts with those of previous studies where high levels of YAP1 overexpression led to sustained proliferation and overgrowth of undifferentiated cells [17, 37]. In any case, the compensatory mechanisms resulting from LIX1 or YAP1 misexpression appeared to lock the determined mesenchyme in a state where the cells were neither proliferative nor differentiated. This state could simply reflect the requirement for a dynamic proliferation event between the determination and differentiation steps. By this hypothesis, because determined LIX1/YAP1-expressing cells are in contact inhibition of proliferation, differentiation could not be initiated. Alternatively, we could speculate that a certain level of YAP1 activity is necessary to initiate SMC differentiation, and because YAP1 activity has been turned off as a consequence of aberrant cell proliferation at the determination stage, differentiation could not be initiated. This second hypothesis highlights the possibility that YAP1 plays a dual role in regulating stomach mesenchyme progenitor development, both during the proliferative phase and later on during the differentiation phase. This hypothesis concords with emerging data showing that YAP1 regulates multiple signalling pathways, such as Wnt, BMP and Notch [38] and Hippo signalling has been shown to regulate Notch signalling [39]. Interestingly, all of these pathways are involved in the development of the GI tract [1,6,19,40-42]. Further investigations are required to examine how YAP1 signalling is integrated in the regulation of SMC differentiation. YAP1 could be cooperating with two different transcription factors to regulate the processes of mesenchyme proliferation and SMC differentiation, similarly to what has recently been described during self-renewal of the intestinal epithelium [28]. In this system, the authors showed that YAP1 cooperates with Klf4 in promoting differentiation of intestinal Goblet cells. Klf4 has been shown to abrogate the expression of Myocardin, a major regulator of SMC differentiation [21], and of Myocardin-induced expression of SMC genes [43], while YAP1 has been shown to interact with Myocardin and interfere with its activity [13].

Conclusion

Altogether, our results demonstrate that LIX1 is a novel and unique marker of digestive mesenchyme immaturity and a regulator of mesenchymal progenitor proliferation and differentiation through its capacity to regulate YAP1 activity and density-dependent proliferation. Additionally, we demonstrate that this activity of LIX1 is conserved in cell culture, suggesting that the mechanism of LIX1 action outlined here is not limited to the developing stomach mesenchyme. These conclusions thus point to the interest of investigating whether the activity of LIX1 is conserved throughout the more general context of organ size control and tissue regeneration. Finally, we have highlighted, through a developmental approach, three properties of LIX1 that could make it essential in cancer research. LIX1 defines an immature state of stomach smooth muscle, regulates cell proliferation within this immature mesenchyme and regulates the activity of the oncogene YAP1. These three properties thus point to the interest of further studies to examine the possible function of LIX1 tumorigenesis and tumour progression.

Example 2

Poor Prognosis of Patients with High Expression of LIX1

Gastrointestinal stromal tumors (GISTs) are the most common mesenchymal neoplasms of the gastrointestinal tract. Since our findings demonstrated that LIX1 is involved in stomach mesenchymal patterning through its capacity to regulate mesenchymal progenitor proliferation and determination, we next examined the expression of LIX1 in GIST cell lines and tissues. First, we found a high level of LIX1 transcripts specifically in GIST882 cells (a GIST cell line homozygous for the oncogenic KIT mutation K641E) (FIG. 1a) (Tuveson et al., 2001). Furthermore, treatment of GIST882 cells with 1 µM of imatinib mesylate or 7.5 µM AKT inhibitor (AKTi), two known inhibitors of KIT (Tuveson et al., 2001; Hapkova et al, 2013), led to the strong and efficient inhibition of LIX1 transcript levels, demonstrating that LIX1 expression in GIST882 cells is dependent upon KIT activity (FIGS. 1Ab and 1Ac).

We next analyzed the tissue expression of LIX1 in normal and GIST samples, by using antibodies specific for human LIX1. Immunochemistry analysis of human colon, using antibodies against LIX1, TMEM16A (a calcium channel expressed in the network of interstitial cells of Cajal) and TUJ1 (anti-neuron specific beta III Tubulin, specifically expressed in ganglion cells). In normal gastrointestinal tissues, LIX1 is strongly expressed in the submucosal and epithelial layers, but faintly in the intestinal wall (Data not shown). Using interstitial cells of Cajal (ICC) and enteric nervous system (ENS) specific markers, we also showed that LIX1 is not detectable in normal ICCs and ENS components. LIX1 mRNA and protein expression in human non-neoplastic stomach muscle and gastric GISTs was performed using in situ hybridization with human LIX1 riboprobe and anti-LIX1 antibodies. Interestingly, analyses for LIX1 expression on paraffin sections revealed that LIX1 mRNA and protein are abnormally expressed in human GISTs arising from the stomach musculature (respectively 20 of 21 cases analyzed and 15 of 21 cases analyzed) (data not shown). LIX1 mRNA and protein expression in the GIST cohort (n=23) ranking from high to negative expression is indicated in Table 1.

TABLE 1

LIX1 mRNA and protein expression in the GIST cohort.

| Expression | GIST-High | GIST-Intermediate | GIST-Low | GIST-Negative |
|---|---|---|---|---|
| LIX1 mRNA | 7/21 (33%) | 9/21 (43%) | 4/21 (19%) | 1/21 (5%) |
| LIX1 protein | 4/21 (19%) | 4/21 (19%) | 7/21 (33%) | 6/21 (28%) |

Figure 1B:
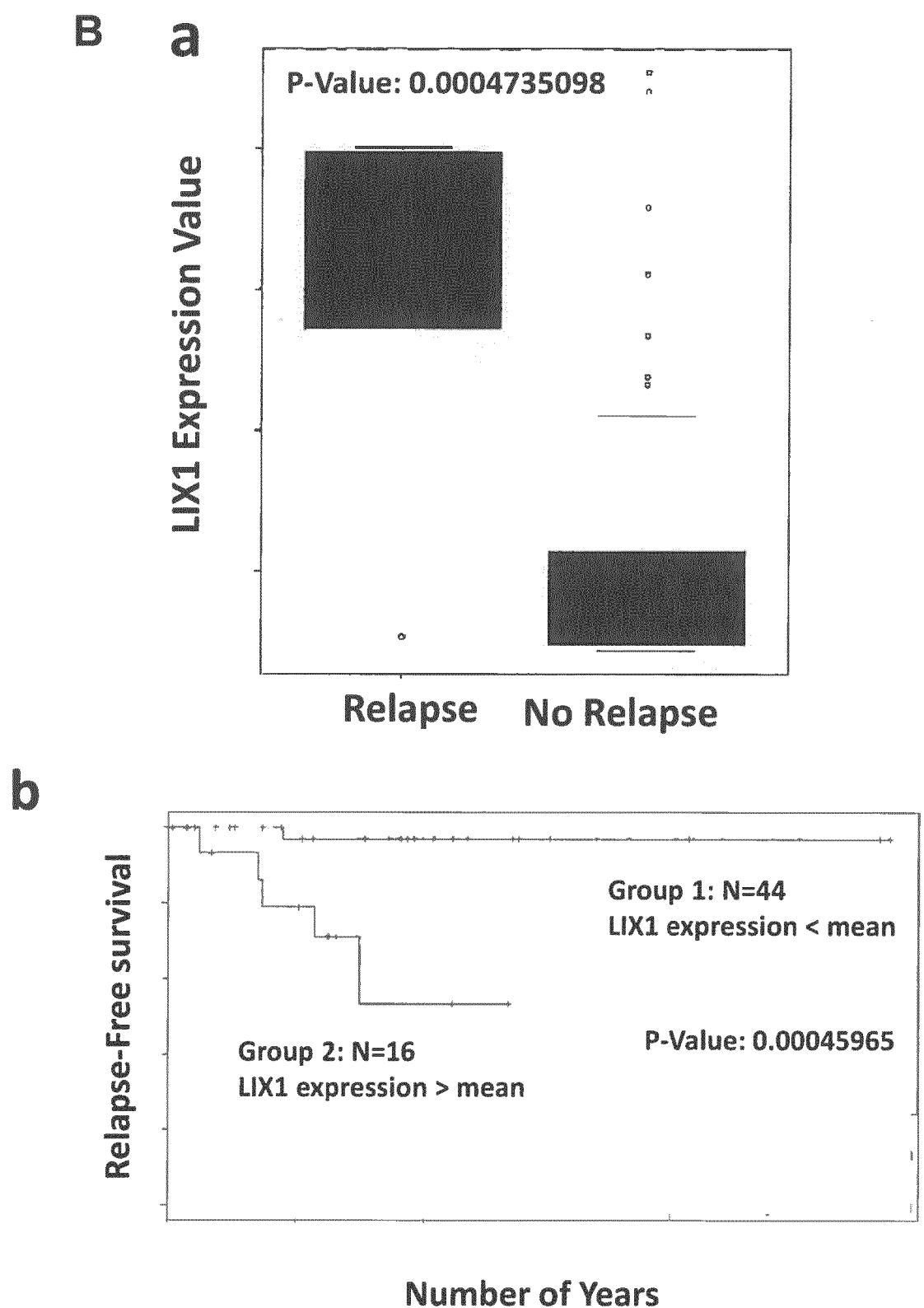

We performed a retrospective analysis and found no statistical correlation, across patients, between LIX1 expression level and mutation status of KIT and PDGFRα. We also analyzed the influence of LIX1 mRNA expression on the relapse of imatinib mesylate-treated GIST patients. We found that high relapse risk is associated with high LIX1 expression (log-rank test, P=0.0005) (FIG. 1Ba). In addition, we evaluated the overall survival of imatinib mesylate-treated GIST patients with a mean follow-up of 58 months. The subject group with high LIX1 expression (n=16) had reduced overall survival compared to the group with low LIX1 expression (n=44) (relative risk=17.669, 95% confidence interval 2.01-154.99, log-rank test, P=0.0005) (FIG. 1Bb). This relationship was specifically observed in GIST patients compared to other sarcoma patients (FIG. 2).

These results demonstrate that LIX1 expression in GIST patients is associated with an unfavorable prognosis.

Discussion

Upon different stimuli, visceral SMCs demonstrate high plasticity, i.e., the capacity to undergo conversion from contractile and functional cells into proliferative cells that are less differentiated (Owens et al, 2004). Our in vivo results demonstrate that, although sustained LIX1 expression stimulates SMC determination, it has a negative impact on further SMC differentiation. Moreover, LIX1 expression in primary differentiated SMC cultures leads to SMC dedifferentiation. Together, these results demonstrate that LIX1 is a newly identified regulator of SMC plasticity. This information and the fact that cell plasticity has often been involved in tumorigenesis (Vicente-Duenas et al, 2009) prompted us to investigate the expression of LIX1 in the most frequent mesenchymal gastrointestinal neoplasms GISTs. Interestingly, we found that LIX1 was expressed in the GIST882 cell line and that treatment of these cells with the KIT and PDGFRA tyrosine kinase inhibitor imatinib mesylate led to decreased LIX1 expression (FIG. 1A). This demonstrates that LIX1 activity could be downstream of the KIT pathway. Moreover, we found that LIX1 expression was abnormally high in GIST tissues, identifying LIX1 as a new marker of GISTs. We found that although a majority of GISTs express high levels of LIX1 mRNA, this did not always correlate with high LIX1 protein expression. This demonstrates that in some GIST cases, LIX1 expression could be mainly due to the immature identity of the GIST tissue, rather than to a specific activity of LIX1 in GIST progression. The correlation between gene expression in normal ICCs and GISTs, in addition to the specific mutations in the KIT gene, have led to the general conclusion that these tumors arise from ICCs (Sanders et al, 2006). However, previous studies have demonstrated that ICCs and SMCs share a common embryological precursor (Torihashi et al, 1997; Klüppel et al, 1998), and that in the adult musculature, they are still capable of trans-plasticity (Torihashi et al, 1998). As we did not detect LIX1 expression in mouse (Chen et al, 2007) and human ICCs (data not shown), and as we demonstrate that LIX1 defines the early population of mesodermally-derived mesenchymal progenitors, we propose that certain GISTs harbor a highly immature phenotype.

In summary, our data identify LIX1 as a novel marker of mesenchymal progenitors and a new regulator of smooth muscle development. Our data thus provide a new tool that could be useful not only in characterizing GISTs, but also in investigating smooth muscle alterations in functional gastrointestinal diseases. We show that LIX1 regulates cell proliferation and SMC plasticity, pointing to the interest of further studies to examine the possible function of LIX1 in GIST tumorigenesis and proliferation.

Example 3

Resistance to tyrosine kinase inhibitors such as imatinib is increasing in GISTs and complete remissions are rare, highlighting the necessity to identify additional therapeutic targets. The inventors investigated the role of LIX1 in secondary imatinib-resistant GISTs using GIST-T1 cells, a primary gastric GIST cell line sensitive to Imatinib treatment that harbors hetereygous deletion in KIT gene with constitutive KIT signaling pathway. LIX1 is expressed in GIST-T1 cells and is upregulated upon Imatinib treatment (FIG. 3).

The inventors established two GIST-T1 cell lines constitutively expressing specific short-harpin directed against LIX1 (ShLIX1-A and ShLIX1-B) and one control GIST-T1 cell line expressing unrelated short-hairpin (ShScramble). Down-regulation of LIX1 expression in GIST-T1 cell line decreases cell proliferation and invasion of GIST-T1 cell line (FIGS. 4 and 6) and increases GIST cell apoptosis (FIG. 5).

The inventors also demonstrated that down-regulation of LIX1 induces a decrease in KIT and YAP/TAZ protein level and activities in GIST-T1 cell (FIG. 7).

REFERENCES

Throughout this application, various references describe the state of the art to which this invention pertains. The disclosures of these references are hereby incorporated by reference into the present disclosure.

1. Le Guen L, Marchal S, Faure S, de Santa Barbara P. Mesenchymal-epithelial interactions during digestive tract development and epithelial stem cell regeneration. Cell Mol Life Sci. 2015; 72:3883-96.

2. Wallace A S, Burns A J. Development of the enteric nervous system, smooth muscle and interstitial cells of Cajal in the human gastrointestinal tract. Cell Tissue Res. 2005; 319:367-82.

3. Gabella G. Development of visceral smooth muscle. Results Probl Cell Differ. 2002; 38:1-37.

4. Owens G K, Kumar M S, Wamhoff B R. Molecular regulation of vascular smooth muscle cell differentiation in development and disease. Physiol Rev. 2004; 84:767-801.

5. Nguyen A T, Gomez D, Bell R D, Campbell J H, Clowes A W, Gabbiani G. Smooth muscle cell plasticity: fact or fiction? Circ Res. 2013; 112:17-22.

6. Notarnicola C, Rouleau C, Le Guen L, Virsolvy A, Richard S, Faure S, De Santa Barbara P. The RNA-binding protein RBPMS2 regulates development of gastrointestinal smooth muscle. Gastroenterology. 2012; 143:687-97.

7. Hapkova I, Skarda J, Rouleau C, Thys A, Notarnicola C, Janikova M, et al. High expression of the RNA-binding protein RBPMS2 in gastrointestinal stromal tumors. Exp Mol Pathol. 2013; 94:314-21.

8. Le Guen L, Notarnicola C, de Santa Barbara P. Intermuscular tendons are essential for the development of vertebrate stomach. Development. 2009; 136:791-801.

9. Sagnol S, Yang Y, Bessin Y, Allemand F, Hapkova I, Notarnicola C, et al. Homodimerization of RBPMS2 through a new RRM-interaction motif is necessary to control smooth muscle plasticity. Nucleic Acids Res. 2014; 42:10173-84.

10. Bando T, Hamada Y, Kurita K, Nakamura T, Mito T, Ohuchi H, Noji S. Lowfat, a mammalian Lix1 homologue, regulates leg size and growth under the Dachsous/Fat signaling pathway during tissue regeneration. Dev Dyn. 2011; 240:1440-53.

11. Swindell E C, Moeller C, Thaller C, Eichele G. Cloning and expression analysis of chicken Lixl, a founding member of a novel gene family. Mech Dev. 2011; 109:405-8.

12. Mao Y, Kucuk B, Irvine K D. Drosophila lowfat, a novel modulator of Fat signaling. Development. 2009; 136: 3223-33.

13. Xie C, Guo Y, Zhu T, Zhang J, Ma P X, Chen Y E. Yap 1 protein regulates vascular smooth muscle cell phenotypic switch by interaction with myocardin. J Biol Chem. 2012; 287:14598-605.

14. An Y, Kang Q, Zhao Y, Hu X, Li N. Lats2 modulates adipocyte proliferation and differentiation via hippo signaling. PLoS ONE. 2013; 8:e72042.

15. Zhao B, Ye X, Yu J, Li L, Li W, Li S et al. TEAD mediates YAP-dependent gene induction and growth control. Genes Dev. 2008; 22:1962-71.

16. Zhao B, Li L, Lei Q, Guan K L. The Hippo-YAP pathway in organ size control and tumorigenesis: an updated version. Genes Dev. 2010; 24:862-74.

17. Halder G, Johnson R L. Hippo signaling: growth control and beyond. Development. 2011; 138:9-22.

18. Choi M C, Ryu S, Hao R, Wang B, Kapur M, Fan C M, Yao T P. HDAC4 promotes Pax7-dependent satellite cell activation and muscle regeneration. EMBO Rep. 2014; 15:1175-83.

19. Faure S, McKey J, Sagnol S, de Santa Barbara P. Enteric neural crest cells regulate vertebrate stomach patterning and differentiation. Development. 2015; 142:331-42.

20. Méricskay M, Blanc J, Tritsch E, et al. Inducible mouse model of chronic intestinal pseudo-obstruction by smooth muscle-specific inactivation of the SRF gene. Gastroenterology. 2007; 133:1960

21. Huang J, Wang T, Wright A C, Yang J, Zhou S, Li L, et al. Myocardin is required for maintenance of vascular and visceral smooth muscle homeostasis during postnatal development. Proc Natl Acad Sci USA. 2015; 112:4447-52.

22. Moniot B, Biau S, Faure S, Nielsen C M, Berta P, Roberts D J, de Santa Barbara P. SOX9 specifies the pyloric sphincter epithelium through mesenchymal-epithelial signals. Development. 2004; 131:3795-804.

23. Chan S W, Lim C J, Chong Y F, Pobbati A V, Huang C, Hong W. Hippo pathway-independent restriction of TAZ and YAP by angiomotin. J Biol Chem. 2011; 286:7018-26.

24. Faure S, Georges M, McKey J, Sagnol S, de Santa Barbara P. Expression pattern of the homeotic gene Bapx1 during early chick gastrointestinal tract development. Gene Expr Patterns. 2013; 13:287-92.

25. Mandler M, Neubuser A. FGF signaling is required for initiation of feather placode development. Development. 2004; 131:3333-43.

26. Gumbiner B M, Kim N G. The Hippo-YAP signaling pathway and contact inhibition of growth. J Cell Sci. 2014; 127:709-17.

27. Liu-Chittenden Y, Huang B, Shim J S, Chen Q, Lee S J, Anders R A et al. Genetic and pharmacological disruption of the TEAD-YAP complex suppresses the oncogenic activity of YAP. Genes Dev. 2012; 26:1300-5.

28. Imajo M, Ebisuya M, Nishida E. Dual role of YAP and TAZ in renewal of the intestinal epithelium. Nat Cell Biol. 2015; 17:7-19.

29. Yu F X, Meng Z, Plouffe S W, Guan K L. Hippo pathway regulation of gastrointestinal tissues. Annu Rev Physiol. 2015; 77:201-27.

30. Zhang Z W, Men T, Feng R C, Li Y C, Zhou D, Teng C B. miR-375 inhibits proliferation of mouse pancreatic progenitor cells by targeting YAP1. Cell Physiol Biochem. 2013; 32:1808-17.

31. Deng J, Lei W, Xiang X, Zhang L, Yu F, Chen J et al. MicroRNA-506 inhibits gastric cancer proliferation and invasion by directly targeting Yapl. Tumour Biol. 2015; 36:6823-31.

32. Zhao B, Wei X, Li W, Udan R S, Yang Q, Kim J et al. Inactivation of YAP oncoprotein by the Hippo pathway is involved in cell contact inhibition and tissue growth control. Genes Dev. 2007; 21:2747-61.

33. Zhou D, Zhang Y, Wu H, Barry E, Yin Y, Lawrence E, et al. Mst1 and Mst2 protein kinases restrain intestinal stem cell proliferation and colonic tumorigenesis by inhibition of Yes-associated protein (Yap) overabundance. Proc Natl Acad Sci USA. 2011; 108:E1312-1320.

34. Bossuyt W, Chen C L, Chen Q, Sudol M, McNeill H, Pan D et al. An evolutionary shift in the regulation of the Hippo pathway between mice and flies. Oncogene. 2014; 33:1218-28.

35. Van Hateren N J, Das R M, Hautbergue G M, Borycki A G, Placzek M, Wilson S A. FatJ acts via the Hippo mediator Yap1 to restrict the size of neural progenitor cell pools. Development. 2011; 138:1893-902.

36. Ito T, Taniguchi H, Fukagai K, Okamuro S, Kobayashi A. Inhibitory mechanism of FAT4 gene expression in response to actin dynamics during Src-induced carcinogenesis. PLoS ONE. 2015; 10:e0118336.

37. Camargo F D, Gokhale S, Johnnidis J B, Fu D, Bell G W, Jaenisch R, Brummelkamp T R. YAP1 increases organ size and expands undifferentiated progenitor cells. Curr Biol. 2007; 17:2054-60

38. Hansen C G, Moroishi T, Guan K L. YAP and TAZ: a nexus for Hippo signaling and beyond. Trends Cell Biol. 2015; 25:499-513.

39. Manderfield L J, Aghajanian H, Engleka K A, Lim L Y, Liu F, Jain R et al. Hippo signaling is required for Notch-dependent smooth muscle differentiation of neural crest. Development. 2015; 142:2962-71.

40. Smith D M, Nielsen C, Tabin C J, Roberts D J. Roles of BMP signaling and Nkx2.5 in patterning at the chick midgut-foregut boundary. Development. 2000; 127:3671-81.

41. Theodosiou N A, Tabin C J. Wnt signaling during development of the gastrointestinal tract. Dev Biol. 2003; 259:258-71.

42. de Santa Barbara P, Williams J, Goldstein A M, Doyle A M, Nielsen C, Winfield S, et al. Bone morphogenetic protein signaling pathway plays multiple roles during gastrointestinal tract development. Dev Dyn. 2005; 234:312-22.

43. Liu Y, Sinha S, McDonald O G, Shang Y, Hoofnagle M H, Owens G K. Kruppel-like factor 4 abrogates myocardin-induced activation of smooth muscle gene expression. J Biol Chem. 2005; 280:9719-27.

44. Hamburger V, Hamilton H L. A series of normal stages in the development of the chick embryo. J Morph. 1951; 88:49-92.

45. Holzmann J, Hennchen M, Rohrer H. Prox1 identifies proliferating neuroblasts and nascent neurons during neurogenesis in sympathetic ganglia. Dev Neurobiol. 2015; 75:1352-67.

The invention claimed is:

1. A method of decreasing proliferation of gastrointestinal stromal tumor (GIST) cells, comprising
   providing to the GIST cells an amount of an LIX1 inhibitor sufficient to decrease proliferation of the GIST cells compared to control cells that do not produce the LIX1 inhibitor, wherein the LIX1 inhibitor is selected from the group consisting of antisense oligonucleotides, siRNAs and ribozymes suitable for blocking the translation of LIX1 mRNA.

2. A method of increasing apoptosis of gastrointestinal stromal tumor (GIST) cells, comprising
   providing to the GIST cells an amount of an LIX1 inhibitor sufficient to increase apoptosis of the GIST cells compared to control cells that do not produce the LIX1 inhibitor, wherein the LIX1 inhibitor is selected from the group consisting of antisense oligonucleotides, siRNAs and ribozymes suitable for blocking the translation of LIX1 mRNA.

3. The method of claim 1, further comprising providing to the GIST cells a tyrosine kinase inhibitor.

4. The method of claim 2, further comprising providing to the GIST cells a tyrosine kinase inhibitor.

* * * * *